(12) United States Patent
Hoffmann et al.

(10) Patent No.: US 9,381,643 B2
(45) Date of Patent: Jul. 5, 2016

(54) DYNAMICAL SYSTEM-BASED ROBOT VELOCITY CONTROL

(71) Applicant: GM GLOBAL TECHNOLOGY OPERATIONS LLC, Detroit, MI (US)

(72) Inventors: Heiko Hoffmann, Simi Valley, CA (US); David W. Payton, Calabasas, CA (US); Derek Mitchell, Calabasas, CA (US)

(73) Assignee: GM Global Technology Operations LLC, Detroit, MI (US)

( * ) Notice: Subject to any disclaimer, the term of this patent is extended or adjusted under 35 U.S.C. 154(b) by 68 days.

(21) Appl. No.: 14/323,047

(22) Filed: Jul. 3, 2014

(65) Prior Publication Data

US 2016/0000511 A1    Jan. 7, 2016

(51) Int. Cl.
*B25J 9/16*    (2006.01)
*G05B 19/19*    (2006.01)

(52) U.S. Cl.
CPC .............. *B25J 9/1628* (2013.01); *B25J 9/1664* (2013.01); *G05B 19/19* (2013.01)

(58) Field of Classification Search
CPC .................. A61B 19/2203; A61B 2019/2207; B25J 9/1628; B25J 9/163; B25J 9/1633; B25J 9/1648; B25J 9/1664; B25J 9/1666; G05B 19/19; G05B 19/402; G05B 19/42–19/427
See application file for complete search history.

(56) References Cited

U.S. PATENT DOCUMENTS

| 4,761,595 A | 8/1988 | Goor |
| 6,266,578 B1 | 7/2001 | Udwadia |
| 2007/0046677 A1 | 3/2007 | Hong et al. |
| 2007/0219668 A1 | 9/2007 | Takahashi et al. |

FOREIGN PATENT DOCUMENTS

DE    102007061323 A1    7/2009

OTHER PUBLICATIONS

Nakanishi et al., "Operational Space Control: A Theoretical and Empirical Comparison", Jun. 2008, The International Journal of Robotic Research, vol. 27, No. 6, pp. 737-757.*
Ijspeert et al., "Dynamical Movement Primitives: Learning Attractor Models for Motor Behaviors", Feb. 2013, Neural Computation, vol. 25, No. 2, pp. 328-373.*

(Continued)

*Primary Examiner* — Spencer Patton
(74) *Attorney, Agent, or Firm* — Quinn Law Group, PLLC

(57) ABSTRACT

A robotic system includes an end-effector and a control system. The control system includes a processor, a dynamical system module (DSM), and a velocity control module (VCM). Via execution of a method, the DSM processes inputs via a flow vector field and outputs a control velocity command. The inputs may include an actual position, desired goal position, and demonstrated reference path of the end-effector. The VCM receives an actual velocity of the end-effector and the control velocity command as inputs, and transmits a motor torque command to the end-effector as an output command. The control system employs a predetermined set of differential equations to generate a motion trajectory of the end-effector in real time that approximates the demonstrated reference path. The control system is also programmed to modify movement of the end-effector in real time via the VCM in response to perturbations of movement of the end-effector.

10 Claims, 2 Drawing Sheets

(56) References Cited

OTHER PUBLICATIONS

Heiko Hoffmann, Peter Pastor, Dae-Hyng Park and Stefan Schaal, "Biologically-inspired Dynamical Systems for Movement Generation: Automatic Real-Time Goal Adaptation and Obstacle Avoidance", May 12, 2009.

Auke Jan Ijspeert, Jun Nakanishi & Stefan Schaal, "Movement Imitation with Nonlinear Dynamical Systems in Humanoid Robots", May 11, 2002.

Auke Jan Ijspeert, Jun Nakanishi and Stefan Schaal, "Learning Attractor Landscapes for Learning Motor Primitives", 2002.

* cited by examiner

DYNAMICAL SYSTEM-BASED ROBOT VELOCITY CONTROL

TECHNICAL FIELD

The present disclosure relates to dynamical system-based robot velocity control.

BACKGROUND

Robots typically include a series of linkages that are interconnected via motor-driven robotic joints. Each robotic joint represents one or more independent control variables/degrees of freedom. End-effectors such as robotic hands or grippers are the particular end linkages in a serial robot which act directly on an object in the performance of a given work task, such as grasping and moving the object. Complex programming and motion control techniques are used in a variety of ways to achieve the required levels of robotic mobility, dexterity, and work task-related functionality. End-effectors approach and depart from a specified goal position according to a particular path or trajectory. Such paths are planned in logic using a variety of approaches. However, conventional end-effector path planning may be less than optimally robust in certain instances as explained below.

SUMMARY

A robotic control system and method are disclosed herein that are suitable for controlling a robotic end-effector. While conventional robots are typically isolated from the surrounding work environment by gates or other barriers, direct interaction between robots and line operators and/or objects located in the robot's work environment is intended with some of the more complex emerging dexterous robot designs. At times, however, unexpected contact may still occur with the end-effector of such robots, which in turn may lead to end-effector perturbations. Such perturbations can cause the end-effector motion to diverge from the planned path, and thus require a more robust control processing functionality.

The present control framework is intended to addresses this particular control challenge via the use of a control system that combines functions of a velocity control module with those of a dynamical system module as explained below. As is well known in the art, end-effector control typically involves programming a controller with predefined approach and departure trajectories in a given task space, e.g., an XYZ Cartesian coordinate frame of reference. The position and velocity of the end-effector are measured and controlled in real time as the end-effector moves toward or away from the specified goal position. Dynamical systems offer an alternative approach. In a dynamical system, the end-effector movement trajectories are not pre-defined. Instead, such trajectories are automatically generated via a controller during a given end-effector movement. Unlike in the continuous closed-loop, programming-intensive control schemes noted above, only a few control commands are specified in a dynamical system. Differential equations ultimately generate the corresponding movement trajectories.

A dynamic movement primitive (DMP) framework may be used to implement such dynamical systems. In a DMP framework, the aforementioned differential equations are adapted to generate given movements. Together, these differential equations can form a library of so-called "movement primitives". However, conventional end-effector control techniques may remain less than optimally robust, particularly when encountering perturbations such as those caused by external forces encountered by the end-effector while moving through planned trajectories.

The control system disclosed herein ultimately generates movement commands for the end-effector, possibly doing so in response to a previously operator-demonstrated work task. The dynamical system module generates desired velocity commands for movement of the end-effector, doing so via a flow vector field. The actual position in free space of the end-effector is measured and transmitted to the dynamical system module as a control input. The control system disclosed herein allows for more diverse or flexible robotic movements relative to the prevailing art, with the robot better able to adapt online or in real time to newly stated goal positions and/or encountering of dynamic or static obstacles in the robot's work environment.

In an example embodiment, a robotic system includes an end-effector and a control system. The control system, which is in communication with the end-effector, includes a processor, a dynamical system module (DSM), and a velocity control module (VCM), with the term "module" as used herein referring to the hardware and software portions of the control system dedicated to performing associated functions as explained below. In particular, the DSM processes a set of inputs and applies the flow vector field, and then outputs a control velocity command. The set of inputs may include a measured or actual position of the end-effector, a desired goal position of the end-effector, and an optional operator-demonstrated reference path of the end-effector, e.g., a path demonstrated via backdriving or teleoperation of the end-effector. The VCM receives or calculates an actual velocity of the end-effector and the control velocity command as inputs, and ultimately generates a motor torque command to the end-effector as an output command.

The control system employs a predetermined set of differential equations to generate a motion trajectory of the end-effector in real time. The motion trajectory approximates the demonstrated reference path. The control system is programmed to adapt or modify movement of the end-effector in real time via the VCM in response to experienced perturbations of movement of the end-effector.

The DSM may include a path transformation module programmed to transform a frame of reference of the flow vector field, and a path blending module that incorporates a tunable linear interpolation term into the differential equations. The tunable linear interpolation term blends together a path of the end-effector drawn forward from a start position with a path drawn backward from a goal position.

The control system appends a flow vector field function with a transform, with the flow vector field function defining the flow vector field noted above. The transform rotates a frame of reference of the flow vector field function to match an orientation of the demonstrated path with an orientation of the new start and goal positions.

The VCM may operate at a cycle rate that is at least five times (5×) higher than a cycle rate of the DSM. For example, the DSM may operate at about 20-40 Hz and the VCM may operate at about 100-1000 Hz, such that the differential equations are updated at the higher frequency.

An associated method includes processing a set of inputs via the DSM having a predetermined flow vector field. The set of inputs includes an actual position of an end-effector of a robotic system, a desired goal position of the end-effector, and a demonstrated reference path of the end-effector. Processing includes employing a predetermined set of differential equations to generate a motion trajectory of the end-effector in real time to approximate the demonstrated reference path. The method also includes outputting a control velocity command via the DSM, and receiving and processing an actual velocity of the end-effector and the control velocity command from the DSM via the VCM. The method may further include generating and transmitting a motor torque command to the end-effector via the VCM to thereby adapt or modify a movement of the end-effector in real time in response to perturbations of movement of the end-effector.

The above features and advantages and other features and advantages of the present invention are readily apparent from the following detailed description of the best modes for carrying out the invention when taken in connection with the accompanying drawings.

DETAILED DESCRIPTION

Figure 1:
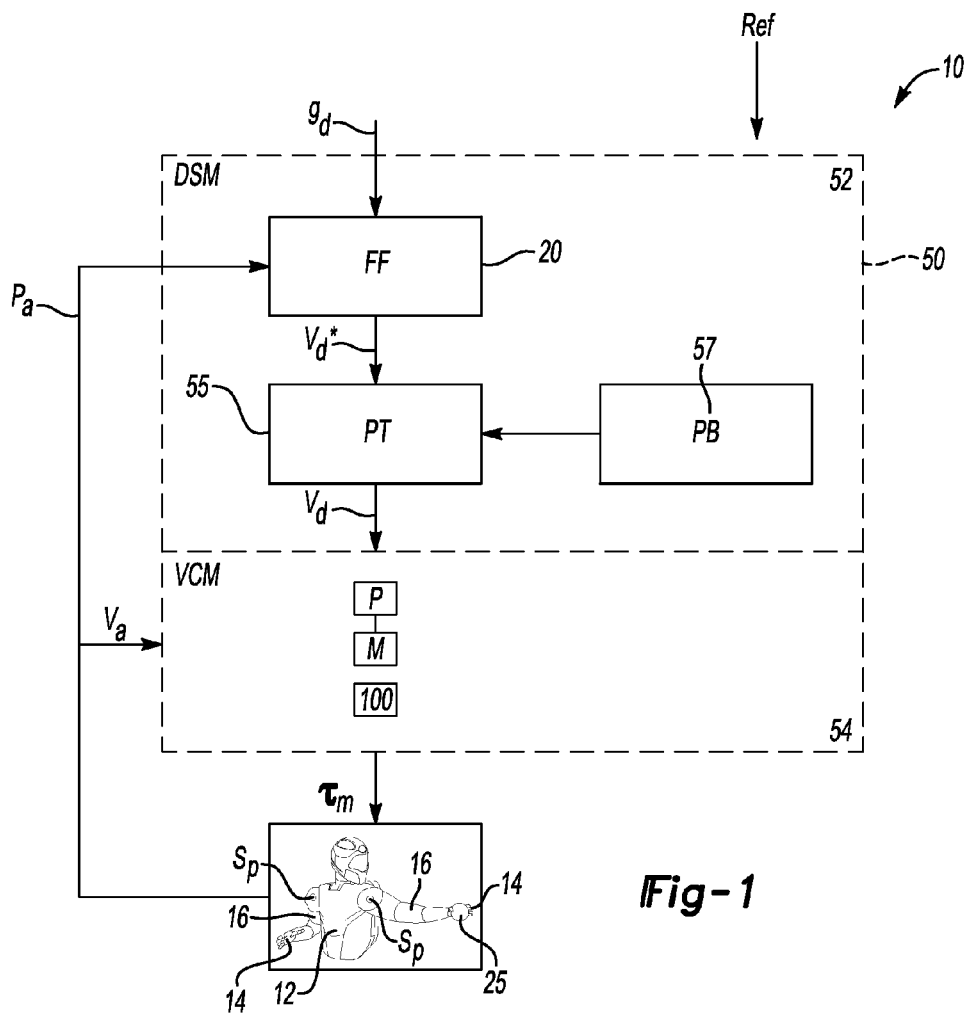
FIG. 1 is a schematic illustration of an example robotic system having a robot with an end-effector, and also having an associated control system with a combined dynamical system module (DSM) and velocity control module (VCM) configured to smooth the movements of the end-effector in the presence of end-effector perturbations.

With reference to the drawings, wherein like reference numbers refer to the same or similar components throughout the several views, a robotic system 10 is shown schematically in FIG. 1. The robotic system 10 includes a robot 12, which is depicted as an example dexterous humanoid robot, but which may be alternatively embodied as any multi-axis robot. The robot 12 includes an end-effector 14 disposed at a distal end of a robot arm 16. Motion of the robot 12, particularly the end-effector 14 and the robot arm 16, is automatically controlled via a control system (C) 50 having an integrated dynamical system module (DSM) 52 and a velocity control module (VCM) 54, the specific programmed functions of which are described in detail below.

The robot 12 is configured in hardware and software to perform one or more automated tasks with multiple control degrees of freedom, and to perform other interactive tasks or control other integrated system components, for instance clamping, relays, task lighting, and the like. In the embodiment shown in FIG. 1, the robot 12 includes a plurality of independently and interdependently-moveable robotic joints to control the motion of the robot arm 16, and ultimately the end-effector 14. Although omitted from FIG. 1 for illustrative simplicity, each robotic joint contains and/or is driven by one or more joint actuators, such as a joint motor, linear actuator, rotary actuator, or the like.

The control system 50 provides precise motion control of the robot 12, including control over the fine and gross movements needed for manipulating an object (not shown) that may be acted on by the end-effector 14. Additionally, the control system 50 provides online movement generation and motor control for the robot 12. As described below, the control system 50 may be programmed to provide dynamic movement primitives or DMPs so as to generate a motion trajectory in real time using differential equations, doing so in a particular manner using the presently disclosed modification that adapt the movements to a large variety of new or unexpected contexts.

In particular, the control system 50 as shown in FIG. 1 may be programmed with a term appended to the differential equations that causes rotation of a generated movement of the end-effector 14, such that the generated movement aligns with new start and end/goal positions in a given end-effector path. The control system 50 also appends an additional term that gradually varies a goal parameter from an original goal position to a new goal position. In other words, known capabilities of DMPs are extended using the present framework such that a single movement of the end-effector 14 or other part of the robot 12 of FIG. 1 can be easily modulated to handle a much larger set of unforeseen circumstances. This approach, which may utilize path transform (PT) logic 55 and path blend (PB) logic 57 to respectively transform the reference frame of a flow vector field and incorporate linear interpolation, is discussed in detail below with reference to FIGS. 3A and 3B.

The control system 50 may be embodied as a computer device or multiple such devices, and is programmed to plan and generate robotic movements of the robot arm 16 and the end-effector 14. The control system 50 may include one or more processors (P) and memory (M), including sufficient amounts of tangible, non-transitory memory. Memory types may include optical or magnetic read only memory (ROM), random access memory (RAM), erasable electrically-programmable read only memory (EEPROM), and the like. The control system 50 may also include a high-speed clock, analog-to-digital (A/D) circuitry, digital-to-analog (D/A) circuitry, and any required input/output (I/O) circuitry and devices, as well as signal conditioning and buffer electronics. Individual control algorithms resident in the controller 50 or readily accessible thereby, such as instructions embodying a method 100 shown in FIG. 5, may be stored in memory (M) and automatically executed via the processor (P) at one or more different control levels to provide the respective control functionality.

Dynamic Movement Primitives

A dynamic movement primitive or DMP, as is well known in the art of robotic control, can be used to generate a particular robotic movement trajectory x(t) with a given velocity v(t). The equations of motion for a DMP are motivated by the dynamics of a damped spring attached to a goal position g and perturbed by a non-linear acceleration:

$$\dot{v}=K(g-x)-Dv+(g-x_0)f(s)$$

$$\dot{x}=v$$

where $x_0$ is the start point of a given movement, K is the spring constant, D is the damping constant, and $f$ is a parameterized non-linear function.

In general, the control system 50 shown in FIG. 1 receives a desired goal $(g_d)$, i.e., a target end position of a given end-effector movement, either via programming or via a reference path provided via demonstration learning, and executes a set of differential equations via the DSM 52. The DSM 52 includes the set of non-linear differential equations as specified below, which are solved via the processor (P). In certain existing systems, differential equations are solved in real time to produce desired joint angles or robot end-effector positions, which are then tracked by another robot controller. Such an approach is conducive to demonstration learning.

However, it is recognized herein that deviations may occur between an actual position and a desired position of the end-effector 14. These deviations are often ignored in conventional end-effector planning. As a result, existing planning approaches may not be possible to use if sufficiently large perturbations are present, such as an external force applied to the end-effector 14, for instance by an object unexpectedly encountered in the workspace of the robot 12 of FIG. 1. In other words, the robot 12 of FIG. 1 may fail to properly track the desired motion of its end-effector 14, and may instead produce an unexpected undesired motion. The control system 50 of the present invention is therefore intended to produce smooth motion of the robot arm 16 and the end-effector 14 in spite of such perturbations.

The DSM 52 shown schematically in FIG. 1 ultimately outputs desired joint velocity ($v_d$), and interacts with the velocity control module (VCM) 54, which in turn sends a commanded motor torque command ($\tau_m$) to the robot 12 and receives an actual joint velocity ($v_a$) from the robot 12. The DSM 52 also receives measured actual joint positions ($P_a$) from the robot 12, e.g., from one or more position sensors $S_p$. As is known in the art, the actual velocity ($v_a$) may be readily calculated from the measured joint positions.

The VCM 54 may be run at a faster rate than the communication rate with the DSM 52, such as at least five times (5×) faster, and as much as fifty times (50×) faster in another embodiment. In an example approach, the DSM 52 may run at a cycle rate of between 20-40 Hz, while the VCM 54 may run at a cycle rate of between 100-1000 Hz. The processor (P) updates the dynamical system equations of the DSM 52 at the higher rate. In the present invention, the DSM 52 creates, for each time step in the movement, a DMP as a movement trajectory, which is defined herein as a desired position (x) and velocity (v) of the end-effector 14. Such a dynamical system can be described as follows, using terms similar to those used above to describe DMPs generally:

$$\dot{v} = K(g-x) - Dv - K(g-x_0)s + Kf(s) + p(x,v)$$

$$\dot{x} = v$$

In the above equations, $x_0$ is the starting position of a movement, g is the desired goal/target of the movement, s is a phase variable that decays exponentially during the movement, K is the spring constant, D is a damping constant, $f$ is an adaptable non-linear function, and p is an optional term that allows the inclusion of an obstacle avoidance technique as set forth below. $f$ may be defined as follows:

$$f(s) = \frac{\sum_i \psi i(s) wi}{\sum_i \psi i(s)} s$$

with $\psi i(s)$ being a Gaussian function. $f$ depends explicitly on the phase variable (s), i.e., $\tau\dot{s} = -\alpha s$, where $\alpha$ is a predefined constant. In other words, the non-linear function $f$ does not depend on time, and therefore $f$ can be simply adjusted such that the equations generate a desired trajectory for the end-effector 14. This is an underlying principle of the discussion that follows with reference to FIGS. 2-4B.

Figure 2:
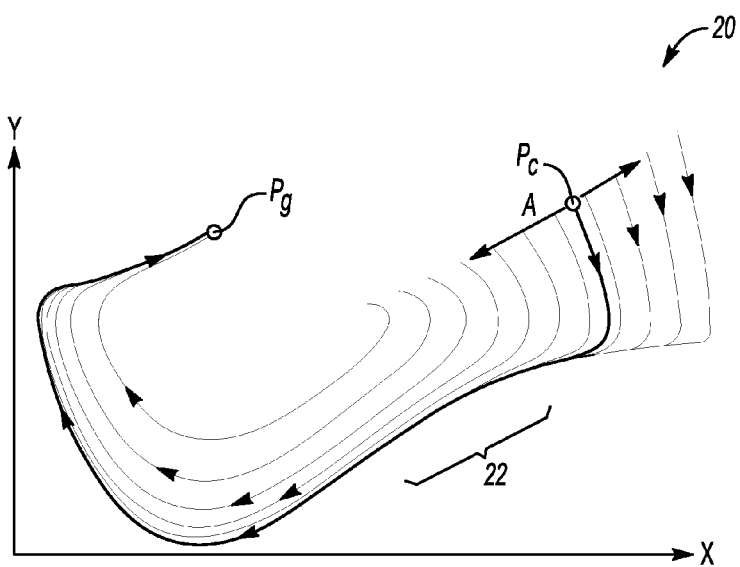
FIG. 2 is a schematic illustration of an example dynamical, differential equation-defined flow vector field usable by the control system of FIG. 1 to properly guide the end-effector of the robot to a goal point.

Referring to FIG. 2, one advantage of the control system 50 of FIG. 1 over the use of a static trajectory is the flexibility provided against perturbations in motion of the end-effector 14, as a desired position/velocity can be readily provided for each location in state space. This advantage also allows the inclusion of obstacle avoidance capabilities, thereby enabling real-time planning of movements around any dynamic, i.e., moving, obstacles in the operating space of the robot 12.

To further illustrate this concept, an example vector flow field (FF) 20 is depicted for perturbations in XY position in state space, with the X axis representing changes in position occurring in the X direction and the Y axis representing changes in position occurring in the Y direction. The flow field 20 acts a velocity vector field, e.g., a field of individual velocity vectors 22, which helps to guide the end-effector 14 from its current position $P_c$ to a goal position $P_g$. Arrow A in FIG. 2 represents the perturbation in different directions.

Referring again to FIG. 1, the control system 50 of FIG. 1 calculates the required motor torque needed to achieve a particular velocity (v) of the end-effector 14. For control of the robot 12, the DSM 52 of FIG. 1 generates the desired velocity $v_d$, which is then converted via the VCM 54 into corresponding control torque $\tau$. In a possible embodiment, the desired velocity ($v_d$) is defined in Cartesian space of the end-effector 14. In such a case, the VCM 54 may be realized mathematically as follows:

$$\tau = PJ^T(x_d - x) + DJ^T(v_d - v)$$

where once again $\tau$ is the commanded control torque, $x_d$ and $v_d$ are the respective desired position and velocity, x and v are the measured position and velocity, J is the Jacobian matrix of the robot arm 16, and P and D are selectable or tunable parameters. The Jacobian J may be computed either inside or outside of the velocity control loop. Alternatively, x and v may describe the motion in joint space as in FIG. 1. In such an instance, the Jacobian J can be omitted.

In an embodiment, the tunable parameter P may be zero or near zero, and thus the control system 50 is dominated by velocity error. Still, the control system 50 will continue to command movements that converge to the desired position ($x_d$), since the position error is provided as feedback to the DSM 52, which in turn is designed to converge at the desired target. The sensor(s) $S_p$ of the robot 12 provide feedback about the actual robot position, e.g., of the end-effector 14. Therefore, the combination of the VCM 54 with the DSM 52 allows for small or zero gains on the position error. This in turn has the advantage of making the movements of the end-effector 14 smoother and more tolerant to perturbations.

The above approach may be further optimized by extending the framework to allow for modulation of the individual dynamic movement primitives. A dynamic movement primitive generates a trajectory in real time using a differential equation, as is known in the art and noted above. The remaining discussion with reference to FIGS. 3A-4B relates to the modifications that can be made to adapt movements of the end-effector 14 to a larger variety of contexts. Particularly, first and second terms are added to the differential equations. The first term rotates a generated movement such that the movement aligns with new desired start and goal positions, while the second term gradually varies a goal parameter from the original goal to a new goal.

An objective of this two-term approach is to provide added flexibility in the generalizing of a human-demonstrated robotic motion to new movement contexts. For instance, a motion in which an object is lifted vertically by the robot 12 of FIG. 1, driven towards a goal position, and dropped cannot be readily generalized using DMPs unless the direction of movement is similar to the demonstrated movement. With the following approach modifications, however, an applied transformation induces a rotational invariance about the vertical axis of movement and generates a similar motion for any approach direction. Additionally, the approach shown in FIGS. 3A-4B offers an approach for adjusting the speed with which a generalized path conforms to the demonstrated path. These additional features introduce added flexibility to existing DMPs that allow a relatively small library of DMPs to represent a much larger range of motion.

With respect to demonstration generally, as is known in the art an input device (not shown) such as a 3D mouse, a joystick, or another control device may be used to teleoperate the robot 12, or the robot 12 may be manually backdriven, through a given work task. That is, the robot 12 may be "taught" to execute a particular work task sequence via human-assisted demonstration of that task. Therefore, the robot 12 may be taught all required grasp positions and approach/departure directions while learning how to grasp an object.

An example of task demonstration/learning is a simple "grasp and lift" task, wherein the robot 12 of FIG. 1 uses its end-effector 14 to grasp and lift an object 25, shown as an example sphere in FIG. 1. An operator of the robot 12 may move the end-effector 14 into a desired position with respect to the object 25, and then correctly grasp the object 27, for instance by manually or automatically actuating the end-effector 14 with sufficient force to establish a desired grasp pose. The operator then moves the robot arm 16 and the end-effector 14 to pick up and move the object 25. Although the robot 12 shown in FIG. 1 could potentially identify task sequences and some relevant perceptual data simply by observing a human operator performing the same task, one of the more challenging aspects of handling new objects and creating new assemblies is determining precisely where to place the end-effector 14. By having a human operator manually move the robot arm 16 and end-effector 14 through each task while the control system 50 records its own raw sensor data, each task demonstration can provide a valuable data stream of experiences from which the robot 12 can ultimately solve these difficult control problems in post-processing subsequent to human-assisted learning.

The robot 12, particularly when embodied as a humanoid robot as shown and operating in the presence of human operators, should be able to adapt quickly in a dynamic environment. Unlike conventional robots that may be access-restricted or protected by a fence, light curtain, or other barrier, a dexterous humanoid may be expected to interact directly with the human operators. Control of such a robot 12 should be sufficiently robust to any uncertainty about the location and pose of the object 25 of FIG. 1. The present approach addresses these challenges by describing robotic movements as flow vector fields/differential equations instead of static trajectories. The flow vector fields are learned via task demonstration, and they generalize to new contexts, such as new start and end positions of a given movement. Such movements are schematically depicted in FIGS. 3A-4B.

The DSM 52 of FIG. 1 may include a path transformation module 55 (PT) and a path blending module 57, which is abbreviated PB in FIG. 1. Again, the term "module" as used here, as well as with respect to the DSM 52 and the VCM 54, refers to a suite of requisite hardware and software needed for performing the designated functions described below. The path transformation module 55 is programmed or otherwise configured to transform the frame of reference of the flow field, e.g., the example flow vector field 20 depicted in FIG. 2. The path blending module 57 incorporates linear interpolation so as to blend together a path drawn forward from a start position ($P_S$) with a path drawn backward from a goal position $P_g$. Tuning of the interpolation provides the ability to select just how quickly an actual path conforms to a path drawn from the goal.

The original dynamical system differential equation may be restated as follows:

$$\dot{v} = K(g-x) - Dv - K(g-x_0)s + Kf(s)$$

Each parameter of the above-stated equation is defined elsewhere above. The path transformation module 55 then modulates this dynamical expression by appending the flow vector field function $f$ with a transform T:

$$\dot{v} = K(g-x) - Dv - K(g-x_0)s + KTf(s)$$

Here, the transform T can have both scalar and rotational components. The transform T can also be set as a function of the decaying phase variable s so as to represent a time-varying transform. By rotating the frame of reference of a flow vector field 20 defined by the function $f$ so as to match the orientation of demonstrated paths with an orientation of a new start and goal, rotational invariance is induced into the generalized motion of the robot 12.

Figure 3A:
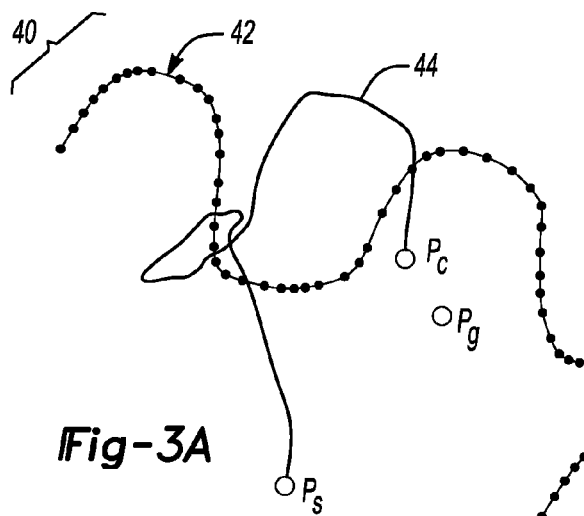
FIG. 3A is a schematic depiction of a demonstrated and a generalized path without the use of example path transformation logic.
Figure 3B:
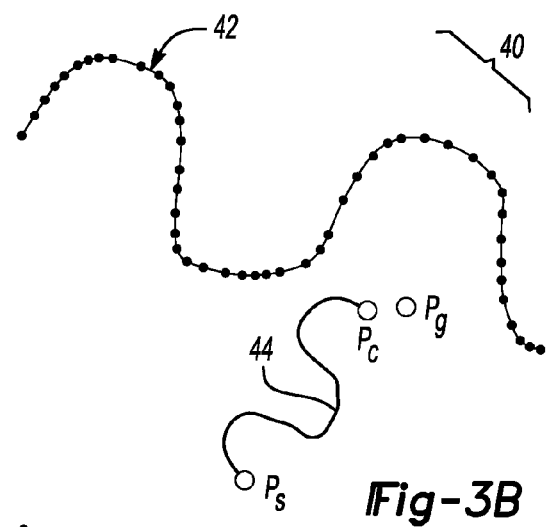
FIG. 3B is a schematic depiction of a demonstrated and a generalized path with use of the example path transformation logic.

FIG. 3A shows such generalized motion trajectories 40 of the end-effector 14 in an example pick and place work task, without the added benefit of the path transformation module 55 shown in FIG. 1. FIG. 3B shows the same motion trajectories 40 after processing via the path transformation module 55. In FIGS. 3A and 3B, the human-demonstrated reference path is trace 42, while the generalized path realized from a start position $P_S$ toward a goal position $P_g$ is depicted as trace 44. The current position of the end-effector 14 is labeled as $P_c$. A comparison of FIGS. 3A and 3B will show that the depiction in FIG. 3B is a more intuitive adaptation of the demonstrated reference path (trace 42).

Implementation of the path blending module 57 of the control system 50 is somewhat more complex. The differential equations are restated as follows:

$$\dot{v} = K(g_m - x) - Dv - K(g_m - x_0)s + Kf(s)$$

$$g_m = g - (g - g_d + x_{od} - x_0)\left(1 - \frac{\ln s}{\ln s_m}\right)$$

where $g_d$ is the goal position of the demonstrated path (trace 44), $x_{0d}$ is the start position of the demonstrated path (trace 44), and the phase variable $s_m$ is an adjustable parameter that determines how quickly the position $g_m$ approaches g, i.e., the desired goal or target position of the movement. The variable $s_m$ can be thought of as the value of the variable s at which $g_m$ and g are equal, and therefore when blending is finished.

Figure 4A:
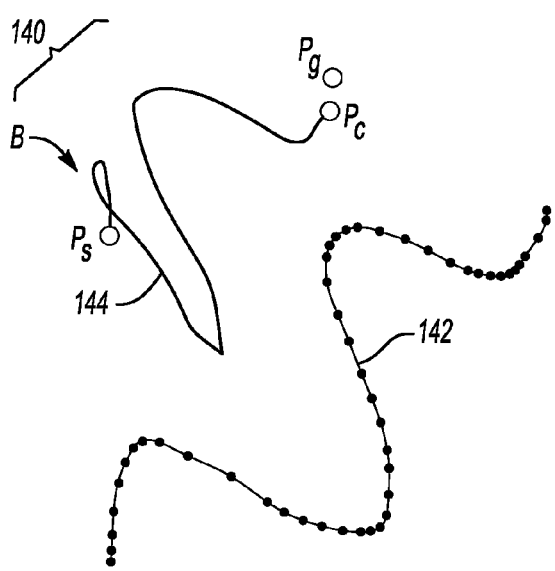
FIG. 4A is a schematic depiction of a demonstrated and a generalized path without the use of example path blending logic.
Figure 4B:
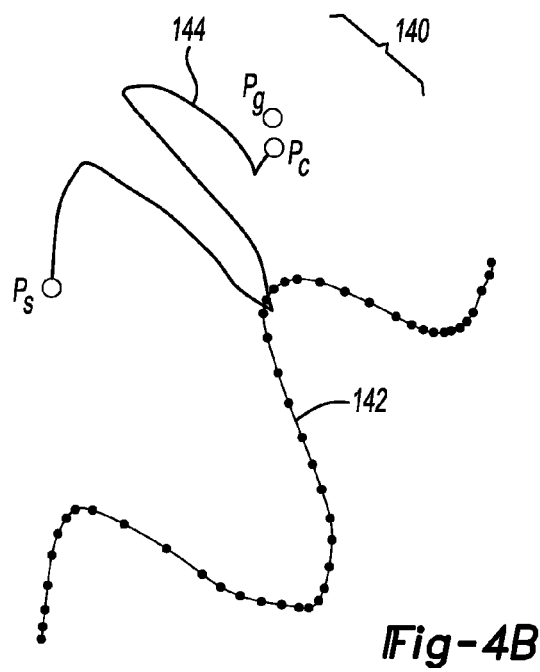
FIG. 4B is a schematic depiction of a demonstrated and a generalized path with the use of the example path blending logic.

FIGS. 4A and 4B depict the effects on the motion trajectories 40 of FIGS. 3A and 3B of path blending when the start position and end goal positions are closer to each other than they are in the demonstrated path (trace 44). FIG. 4A shows motion trajectories 140 with a generalized path 144 without the benefit of blending via the path blending module 57, while FIG. 4B shows the same generalized path 144 after such blending. Note that in FIG. 4B, processing via the path blending module 57 causes the generalized path 144 of the motion trajectories 140 to maintain the structure of the demonstrated path 142 without causing the robot 12 to move backward, as it does in FIG. 4A as indicated by arrow B. Adjusting the variable $s_m$ in this case will scale the shape of the path between the generalized paths 144 in FIGS. 4A and 4B.

Figure 5:
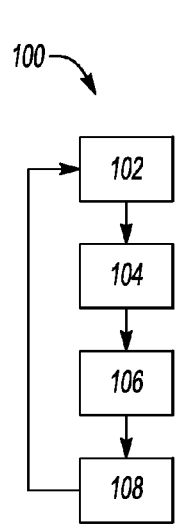
FIG. 5 is a flow chart describing an example method of using the control system shown in FIG. 1.

Referring briefly to FIG. 5, a method 100 of using the above-described control system 50 begins with step 102. Step 102 may entail processing a set of inputs via the DSM 52 and its predetermined flow vector field 20. As noted above, such inputs may include the actual position $P_X$ of the end-effector 14 of the robotic system 10, as well as a desired goal position ($g_d$) of the end-effector 14 and possibly a demonstrated reference path of the end-effector 14. Step 102 includes employing a predetermined set of differential equations to generate a motion trajectory of the end-effector 14 in real time to approximate a demonstrated reference path.

At step 104, the control system 50 of FIG. 1 outputs a desired control velocity command $V_d$ via the DSM 52. The method 100 then proceeds to step 106, where the VCM 54 receives and processes an actual velocity $V_a$ of the end-effector and the control velocity command $V_d$ from the DSM 52.

At step 108, the VCM 54 generates and transmits a motor torque command $\tau_M$ to the end-effector 14 to thereby adapt or modify a movement of the end-effector 14 in real time in response to perturbations of movement of the end-effector 14.

The above-described control system 50 and method 100 thus provides a generic approach toward controlling the movement for any type of end-effector or other robotic manipulator. Using flow vector fields specifically defined by the modified differential equations described herein, desired velocities are computed in a manner that accounts for any perturbances of the end-effector 14. In this manner, the disclosed invention seeks to improve upon conventional DMPs by extending the framework to allow for modulation of individual primitives.

While the best modes for carrying out the invention have been described in detail, those familiar with the art to which this invention relates will recognize various alternative designs and embodiments for practicing the invention within the scope of the appended claims.

The invention claimed is:

1. A robotic system comprising:
    an end-effector; and
    a control system in communication with the end-effector, including:
        a processor;
        a dynamical system module (DSM) which processes a set of inputs via a flow vector field and outputs a control velocity command, wherein the set of inputs includes an actual position of the end-effector, a desired goal position of the end-effector, and a demonstrated reference path of the end-effector; and
        a velocity control module (VCM) in communication with the dynamical system module, wherein the velocity control module receives an actual velocity of the end-effector and the control velocity command as inputs, and generates a motor torque command to the end-effector as an output command;
    wherein the control system employs a predetermined set of differential equations to generate a motion trajectory of the end-effector in real time that approximates the demonstrated reference path, and wherein the control system is programmed to adapt or modify a movement of the end-effector in real time via the velocity control module in response to perturbations of movement of the end-effector, and wherein the DSM includes a path transformation module programmed to transform a frame of reference of the flow vector field, and also includes a path blending module that incorporates a tunable linear interpolation term into the differential equations so as to blend together a path of the end-effector drawn forward from a start position with a path drawn backward from a goal position.

2. The robotic system of claim 1, wherein the control system is operable to append a flow vector field function defining the flow vector field with a transform that rotates a frame of reference of the flow vector field function to match an orientation of the demonstrated path with an orientation of new start and goal positions.

3. The robotic system of claim 1, wherein the end-effector is a robotic gripper.

4. The robotic system of claim 1, wherein velocity control module operates at a cycle rate that is at least 5× higher than a cycle rate of the dynamical system module.

5. The robotic system of claim 4, wherein the cycle rate of the dynamical system module is 20-40 Hz and the cycle rate of the velocity control module is 100-1000 Hz.

6. A method comprising:
    processing a set of inputs via a dynamical system module (DSM) having a predetermined flow vector field, including an actual position of an end-effector of a robotic system, a desired goal position of the end-effector, and a demonstrated reference path of the end-effector, wherein processing the set of inputs includes employing a predetermined set of differential equations to generate a motion trajectory of the end-effector in real time to approximate the demonstrated reference path;
    outputting a control velocity command via the dynamical system module;
    receiving and processing an actual velocity of the end-effector and the control velocity command from the dynamical system module via a velocity control module (VCM);
    generating a motor torque command to the end-effector via the velocity control module to thereby adapt or modify a movement of the end-effector in real time in response to perturbations of movement of the end-effector; and
    transforming a frame of reference of the flow vector field via a path transformation module of the control system, and incorporating a tunable linear interpolation term into the differential equations via a path blending module of the control system so as to blend together a path of the end-effector drawn forward from a start position with a path drawn backward from a goal position.

7. The method of claim 6, further comprising appending a flow vector field function defining the flow vector field with a transform that rotates a frame of reference of the flow vector field function to thereby match an orientation of the demonstrated path with an orientation of new start and goal positions.

8. The method of claim 6, wherein transmitting a motor torque command to the end-effector includes transmitting a motor torque command to a robotic gripper.

9. The method of claim 6, further comprising operating the velocity control module at a cycle rate that is at least 5× higher than a cycle rate of the dynamical system module.

10. The method of claim 9, wherein the cycle rate of the dynamical system module is 20-40 Hz and the cycle rate of the velocity control module is 100-1000 Hz.

* * * * *